United States Patent
Renders et al.

[11] Patent Number: 6,138,679
[45] Date of Patent: Oct. 31, 2000

[54] METHOD SUITABLE FOR INFLUENCING THE INGESTION OF FOOD BY HUMANS VIA THE MOUTH CAVITY

[76] Inventors: Johannes Bonefatio Th. M. Renders, Griekenwag 24, Oss, Netherlands, 5342 PZ; Renatus Wilhelmus G. Linders, Maasstraat 14, Uden, Netherlands, 5404 ND

[21] Appl. No.: 09/180,686
[22] PCT Filed: May 6, 1997
[86] PCT No.: PCT/NL97/00256
§ 371 Date: Nov. 13, 1998
§ 102(e) Date: Nov. 13, 1998
[87] PCT Pub. No.: WO97/42916
PCT Pub. Date: Nov. 20, 1997

[30] Foreign Application Priority Data

May 15, 1996 [NL] Netherlands ............................ 1003122

[51] Int. Cl.⁷ ................................................. A61B 17/24
[52] U.S. Cl. ............................ 128/897; 433/19; 128/848
[58] Field of Search .................................. 128/897, 898, 128/848; 600/300, 23, 24; 434/262, 263, 264; 601/38; 433/6, 19, 215

[56] References Cited

U.S. PATENT DOCUMENTS

| 2,604,093 | 7/1952 | Orth | 128/848 |
| 4,472,139 | 9/1984 | Rosenberg | 433/19 |
| 4,727,867 | 3/1988 | Knoderer . | |
| 4,842,519 | 6/1989 | Dworkin | 433/215 |
| 5,284,161 | 2/1994 | Karell | 128/848 |
| 5,490,520 | 2/1996 | Schaefer et al. | 128/848 |

FOREIGN PATENT DOCUMENTS

| 374163 | 4/1923 | Germany . |
| 1602507 | 10/1990 | U.S.S.R. . |
| WO86/01706 | 3/1986 | WIPO . |

*Primary Examiner*—John P. Lacyk
*Assistant Examiner*—Joseph A. Cadugan
*Attorney, Agent, or Firm*—Jacobson, Price, Holman & Stern, PLLC

[57] ABSTRACT

A device suitable for influencing the ingestion of food via the mouth cavity of humans. The capacity of the mouth cavity is reduced with a view to reducing the body weight. This is accomplished by limiting the maximum degree to which the lower jaw can be opened.

29 Claims, 6 Drawing Sheets

METHOD SUITABLE FOR INFLUENCING THE INGESTION OF FOOD BY HUMANS VIA THE MOUTH CAVITY

FIELD OF THE INVENTION

The invention relates to a method suitable for influencing the ingestion of food via the mouth cavity of humans, wherein connecting means are provided between the upper jaw and the lower jaw, which connecting means impede the opening movement of the lower jaw. The invention furthermore relates to means for carrying out said method.

BACKGROUND OF THE INVENTION

From SU-A-1,602,507 a device for limiting the width of the mouth opening is known, wherein two rings are provided between the upper teeth and the lower teeth, which rings limit the degree to which the lower jaw can be opened. These rings may be used in the treatment of badly functioning lower jaw joints.

In modern times, where slimness is considered an ideal and obesity constitutes a major problem for many people. Obesity is furthermore a problem which may jeopardize people's health.

A large number of therapies are known for reducing the amount of weight and help people to slim down. Many of these therapies are based on following certain diets, whereby it is attempted either to reduce the amount of food that is being ingested, or to regulate the ingestion of food in such a manner that particular foodstuffs are avoided. Other known therapies are based on the use of pharmaceutical agents which act on the digestive system.

A drawback of these known therapies is the fact that it is often difficult for people to follow or keep up a diet. Another drawback is the fact that in many cases undesirable substances are introduced into the body along with said pharmaceutical agents, which substances may have less desirable side effects.

Assuming that in many cases obesity is to a large degree caused by excessive ingestion of food, it is known to render the jaws of bulimia patients immovable, after which food can only be ingested in a very special manner and in liquid form. Of course such a method cannot be used for normal people who wish to slim down or reduce their weight.

SUMMARY OF THE INVENTION

The present invention is based on the consideration that in order to reduce an amount of weight it is desirable to influence the amount of food to be ingested via the mouth cavity. An object of the invention is to provide a method by which the ingestion of food can be made more difficult.

In order to accomplish this objective the method according to the invention is characterized in that said connecting means co-operate with further means present in the mouth cavity, so that when the lower jaw is opened beyond a predetermined limit, a signal is generated, as a result of which the lower jaw is prevented from opening any further. The invention is thereby based on the insight that many people who suffer from obesity, often eat too quickly and too greedily, consequently the ingestion of food takes place in too short a time, as a result of which they do not experience a feeling of satisfaction.

By limiting the degree to which the lower jaw can be opened, it is accomplished that food and beverages can only be taken in small bites and sips, as a result of which the total time spent on the ingestion of food is increased and the digestive system is given the chance to adjust to the food being ingested, so that a sense of hunger will disappear, in spite of a reduced amount of food being ingested, and the need for ingesting large amounts of food will disappear. It has become apparent that all this has a very advantageous effect with regard to achieving the proper body weight. Furthermore it has become apparent that because there is no longer any quick ingestion of large amounts of food, the glucose level in the blood will no longer exhibit a peak but instead will obtain a much more constant trend.

Another advantageous aspect of the invention is the fact that the swallowing pattern is influenced by the reduced mouth opening, in the sense that it is no longer possible to swallow large amounts of food at a time, so that swallowing must take place in small measures. It has become apparent that when the method according to the invention is used, the person in question will continue to eat less quickly after removal of the means that have been placed in the mouth cavity. Of course there is a possibility that the person who uses the method according to the invention for some time and subsequently stops using it, will start to eat quickly again after sometime. In that case the method must be repeated.

According to an advantageous embodiment of the method according to the present invention said further means are mechanical means, by which a sensory stimulus and/or a pain stimulus is generated at a sensitive place in the mouth cavity.

In another embodiment said further means comprise electric and/or electronic means, by which a sound signal, a vibration signal or a pain signal is generated. In both cases said further means are thereby designed such that said signal is generated when the lower jaw is opened to a predetermined degree, thus preventing the lower jaw from being opened any further, so that only small amounts of food can be ingested per time unit.

According to another advantageous embodiment, wherein said connecting elements are made up of one or more bar-shaped elements, each bar-shaped element is provided, at least at one end, with a flanged part or a thickening, which fits in the space between the jawbone and the cheek, and wherein the upper and/or the lower teeth are provided with an element which engages around each bar-shaped element and which is capable of sliding movement over said bar-shaped element, all this in such a manner that when the lower jaw is opened, said flanged part or said thickening is pressed against a sensitive part of the jaw. The thickenings or the flanged part of the bar-shaped element are thereby accommodated in the space between the cheek and the jaw, and said thickenings have some play within said space, in the direction in which the lower jaw opens, whereby said thickenings function as stops against the jawbone and generate a pain stimulus when the lower jaw is opened to a predetermined degree.

In another embodiment each bar-shaped element is fixed to the upper teeth or the lower teeth with one end, and is provided with said flanged part or said thickening at its other end. Also in this embodiment the flanged part or the thickening is pressed against the jawbone when the lower jaw is opened, so that a pain signal is generated.

An advantageous embodiment of the method according to the invention is characterized in that said connecting means are made up of at least one flexible cord or wire, which is fixed to the lower teeth or to the upper teeth with one end, and in that said further means are made up of at least one element, to which the other end of said cord or said wire is connected in such a manner that the tensioned cord or wire will press the element against the upper jaw or the lower jaw when the jaws are opened.

In an embodiment of the above-described method said at least one element is a pivoting element provided on said upper teeth or said lower teeth, to which said cord or said wire is connected with its other end, and which is provided with a bar-shaped part, which exhibits a flanged part or a thickening at its end, which is moved towards the jawbone by the pivoting movement of the element. When the jaws are opened the cord will be tensioned, and the pivoting element will be pivoted, as a result of which the flanged part or said thickening will be pressed against the jawbone, causing it to generate a signal which warns the user not to open his jaws any further, thus providing an impediment with regard to the ingestion of food. The flanged part or the thickening may act directly on the jawbone thereby, generating a pain stimulus. Furthermore it is possible to have said flanged part or said thickening co-operate with an electric/electronic component provided on the jawbone. In one embodiment said component may be a switch element, which is incorporated in an electric circuit comprising a voltage source and electrodes for delivering an electric shock to a sensitive part of the mouth cavity.

According to another embodiment it is also possible to incorporate into the electric circuit means for generating a sound signal or a vibration signal instead of electrodes for delivering an electric shock signal. All these signals warn the user not to open his mouth beyond a predetermined limit, as a result of which the ingestion of food is impeded.

In another advantageous embodiment said electric/electronic component is made up of a stack of one or more piezo-electric plates, which generate an electric voltage when a pressure is exerted thereon, which voltage is applied to a sensitive part of the mouth cavity.

Another advantageous embodiment is characterized in that said further means are made up of at least one wire-like element, which is provided around the upper jaw or the lower jaw, and whose ends are connected to a cord or wire which is provided on either side of the mouth cavity and which is turned around guide elements on the upper teeth or the lower teeth. Said wire-shaped element may thereby be provided with local thickenings, which transfer the tension force in said wire-like element locally to the jawbone, thus generating a pain stimulus or a sensory stimulus at that location, as a result of which the user is warned again that it is not desirable to open his jaw any further.

The invention furthermore relates to means for carrying out the method, which means are indicated in more detail in the claims and which will be explained in more detail hereafter with reference to the drawing, which show diagrammatic examples of said means.

DETAILED DESCRIPTION OF THE PREFERRED EMBODIMENTS

It is noted that the Figures only show those parts of the mouth cavity that are necessary for a proper understanding of the invention.

Figure 1:
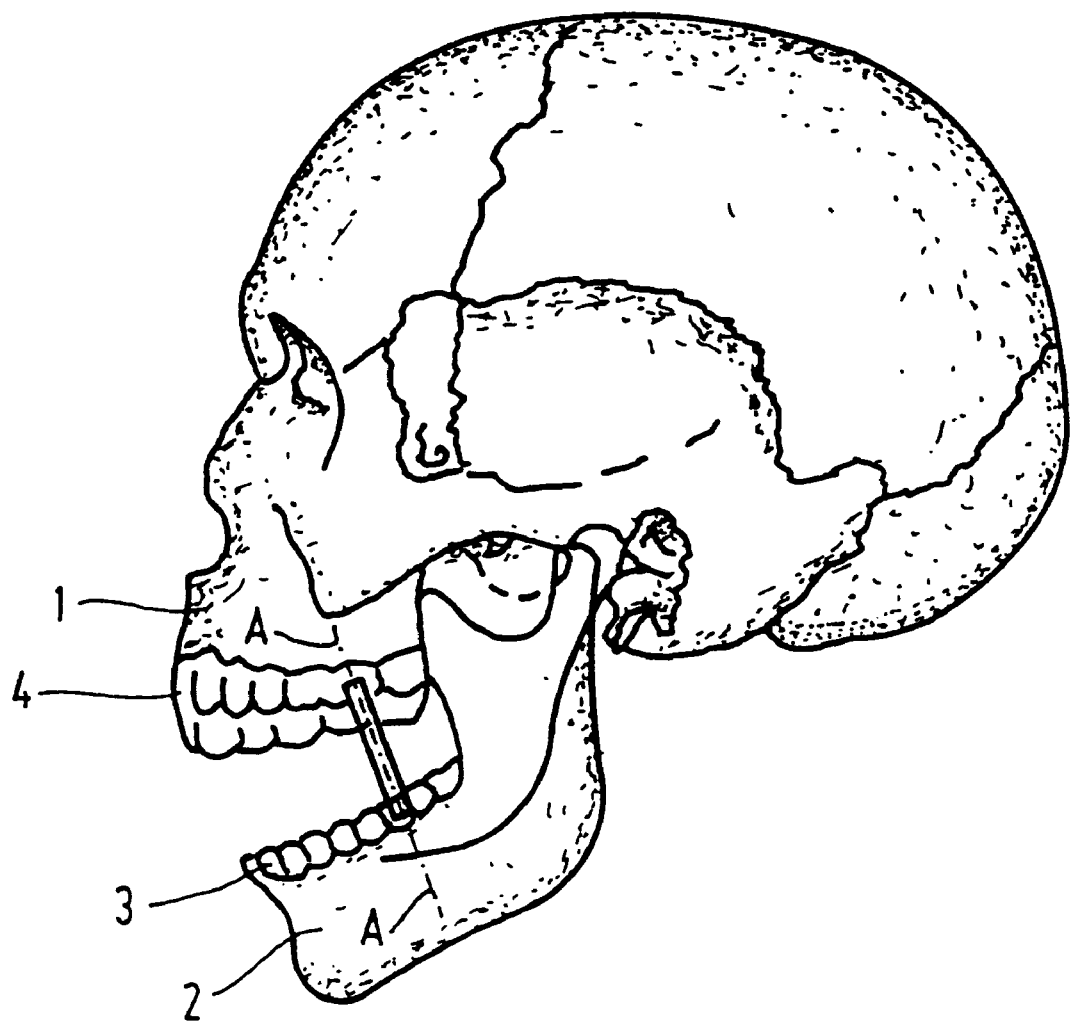
FIG. 1 is a diagrammatic view of a skull with jaws in an opened condition.

In FIG. 1 numeral 1 indicates an upper jaw, and numeral 2 indicates a lower jaw, which occupies an opened position with respect to said upper jaw. The lower jaw and the upper jaw are provided with lower teeth 3 and upper teeth 4 respectively in a known manner.

Figure 2:
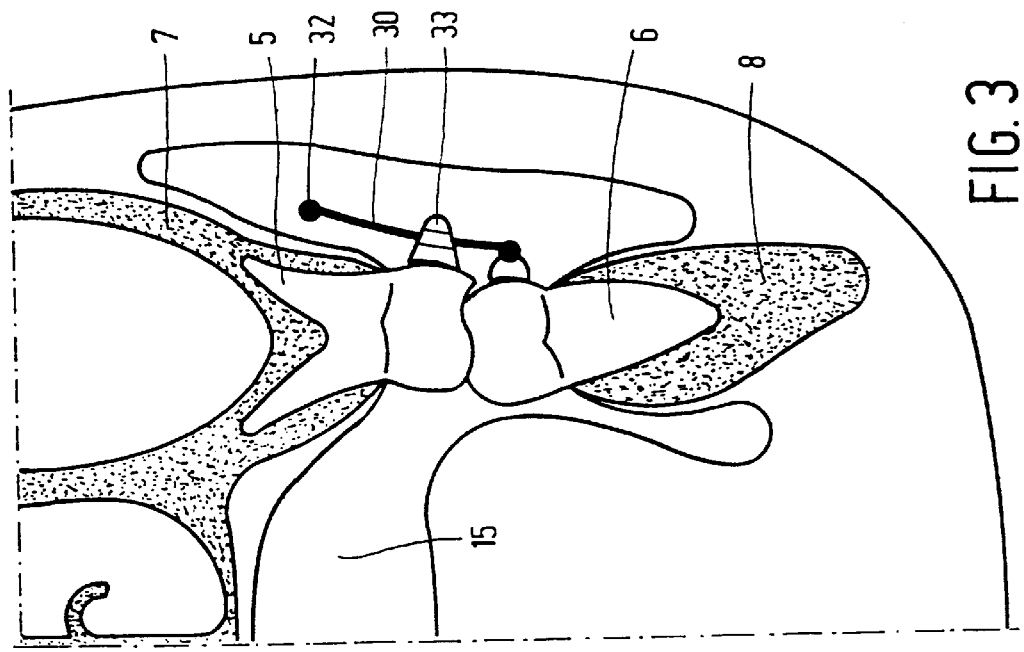
FIGS. 2 and 3 are diagrammatic views, not to scale, of a mouth cavity according to line A—A in FIG. 1, wherein the upper jaw and the lower jaw are connected by means of bar-shaped elements.

FIG. 2 diagrammatically shows part of the mouth cavity shown in FIG. 1, wherein a bar-shaped element 20 is provided between upper jaw 7 and cheek 11 and also between lower jaw 8 and said cheek 11, which bar-shaped element 20 is provided with thickenings 21 and 22 at its ends, which are accommodated in the space between cheek 11 and upper jaw 7 and lower jaw 8 respectively.

Sliding elements 23 and 24 are provided on teeth 5 and 6 respectively, which elements engage around bar 20 and which are capable of sliding movement thereby thereover. Sliding elements 23 and 24 keep bar-shaped element 20 in position. The thickened ends 21 and 22 of said bar-shaped element are provided in the cavities between the jaws and the cheek with some play, but bar 20 is thereby configured such that said thickenings will make contact with the respective parts of the lower jaw and the upper jaw when lower jaw 8 is opened, so that the thickenings will exert a certain pressure on the jaws when the lower jaw is opened to a predetermined degree. As a result a sense of pain will occur and further opening of the jaw is limited. In this manner the maximum degree to which the jaws can be opened with respect to each other can be determined by suitably selecting the length and the shape of the bar-shaped elements. As a result of this the maximum capacity of the mouth cavity 15 will be reduced, which has the advantage that the person in question will take smaller bites than normally, the ingestion of food will thereby have to take place over a longer period of time. As a result of this that person's hunger will be satisfied sooner and the total ingestion of food will be reduced.

Figure 3:
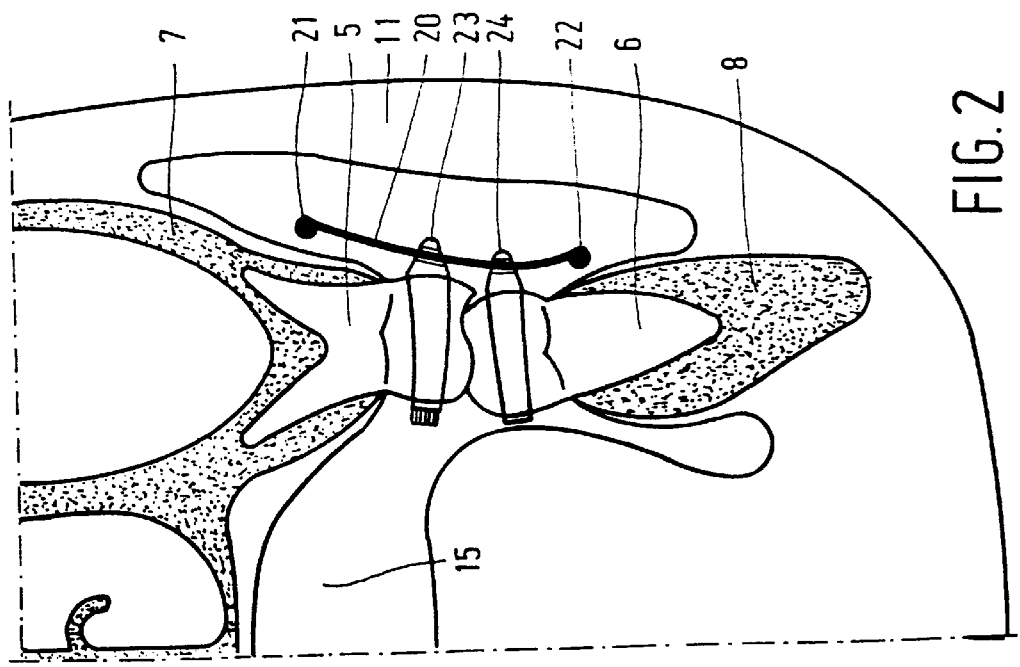

FIG. 3 diagrammatically shows an embodiment which also uses bar-shaped elements. In this embodiment bar-shaped elements 30 are provided on either side of the mouth cavity 15, which bar-shaped elements are fixed to the teeth 6 of the lower jaw at their lower sides and which are provided with a thickening 32 at their upper sides. Teeth 5 of the upper jaw are provided with sliding elements 33, which engage around bar-shaped element 30 and which are capable of sliding movement thereover. This will press bar thickening 32 against the upper jaw at some stage during the opening of the lower jaw, thus generating a pain signal and preventing said lower jaw from being opened any further. By suitably selecting the length of bar 30 the maximum opening of the lower jaw is limited again, thus reducing the capacity of the mouth cavity 15.

Figure 4:
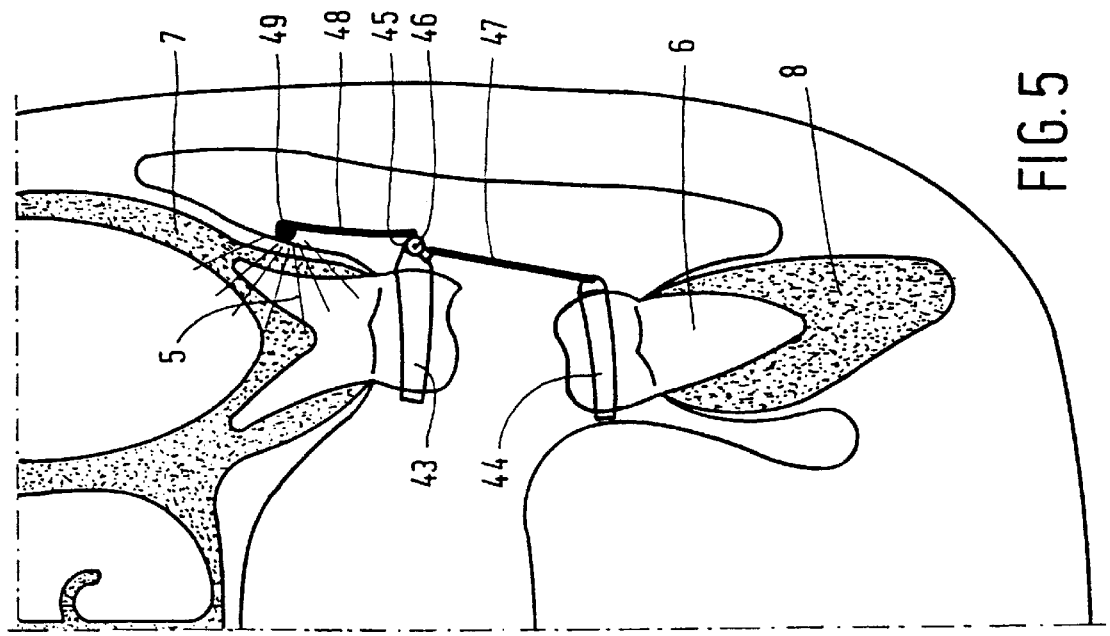
FIGS. 4 and 5 are diagrammatic, partly sectional views of a mouth cavity, wherein the upper jaw and the lower jaw are connected by means of a wire, which acts on a pivoting bar-shaped element.
Figure 5:
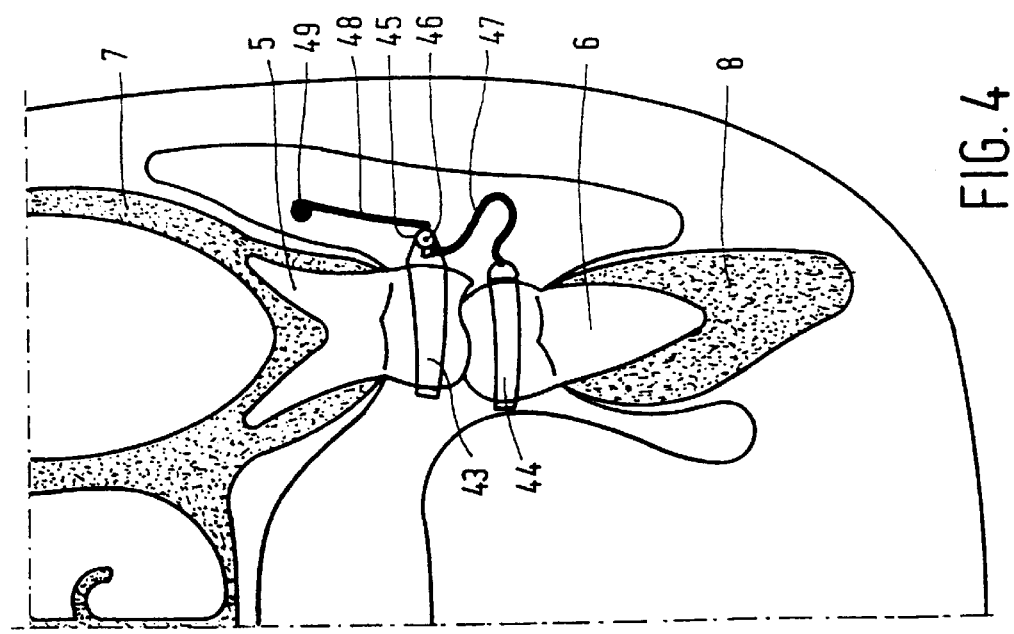

FIGS. 4 and 5 are partial sectional views of a mouth cavity which show the closed and the open position of the jaws respectively. Fastening elements 43 and 44 are provided on teeth 5 and teeth 6 of the upper jaw and the lower jaw respectively. Fastening element 43 is thereby provided with a pivoting element 45, which pivots about a pivot point 46. On the one hand a wire or cord 47 is connected to said pivoting element 45, which is connected to the fastening element 44 on teeth 6 of the lower jaw with its other end. On the other hand a bar-shaped element 48 is connected to said pivoting element 45, which bar-shaped element is provided with a thickening 49 at its upper side. When lower jaw 8 is opened, cord 47 will be pulled taut, as a result of which pivoting element 45 will pivot about its pivot point and bar 48 will be pulled towards upper jaw 7. This will cause thickening 49 to be pressed against the jaw, as a result of which a pain stimulus will occur and the opening movement of the jaws will be impeded. It is noted that a spring (not shown) is provided on pivot point 46, which spring exerts a force on pivoting element 45 and/or on bar-shaped element 48, which force causes element 48 to move away from the jaw. All this is done in such a manner that the thickening 49 is not in contact with the jawbone in the closed condition of the jaws.

Figure 7:
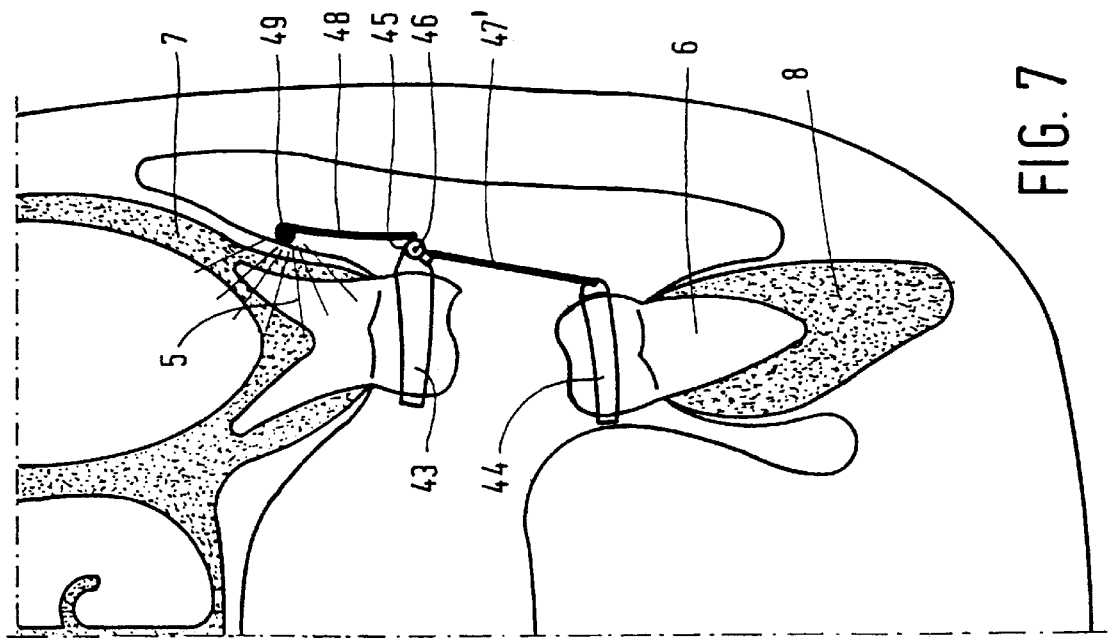
FIGS. 6 and 7 show an embodiment similar to the one shown in FIGS. 4 and 5, with the understanding that in this embodiment a wire is used which is made of a memory material.
Figure 6:
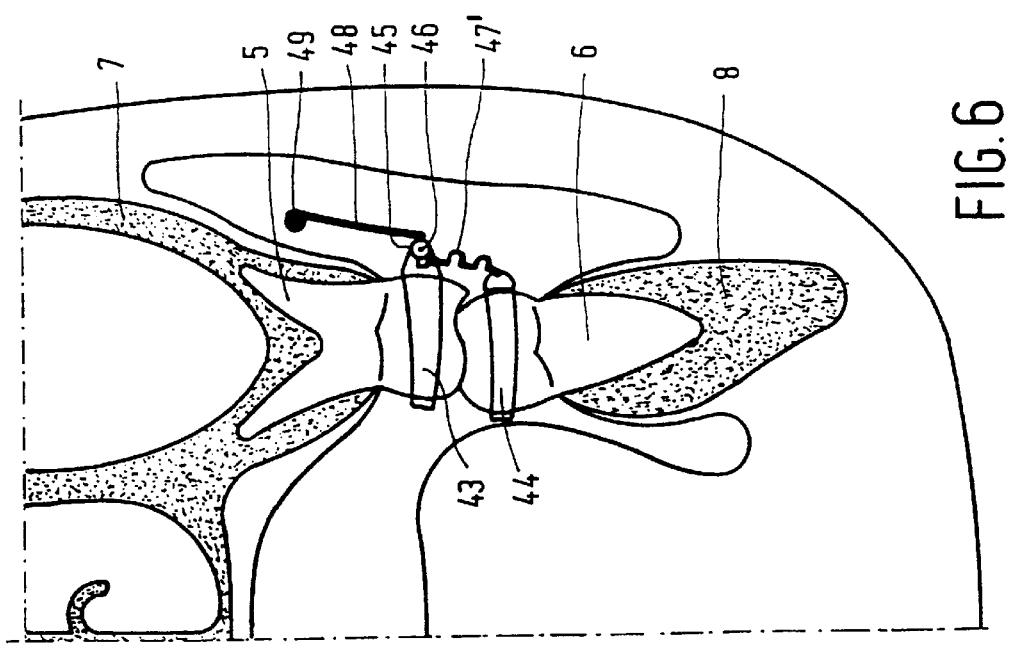

In the embodiment shown in FIGS. 4 and 5 said wire or cord is in the shape of a flexible element. There is a chance that said cord might land between the teeth when the jaws are being closed. In order to avoid this, connecting element 47 is a wire of a memory material in the embodiment of FIGS. 6 and 7, which wire is provided with one or more bulges extending transversely to the longitudinal direction. When the jaws are opened, a wire of this type will be pulled straight as indicated in FIG. 7, whilst closing of the jaws will cause the wire to return to its original, shorter form as a result of the action of the memory material. The wire may also have a shape other than a wire comprising bulges. It may be a coil spring, for example. Also in this embodiment pivoting element 45 will be provided with a spring (not shown), which exerts a force on pivoting element 45 or bar 48 in a direction away from the jawbone, so that thickening 49 will not be in contact with the jawbone in the closed condition of the jaws.

Figure 9:
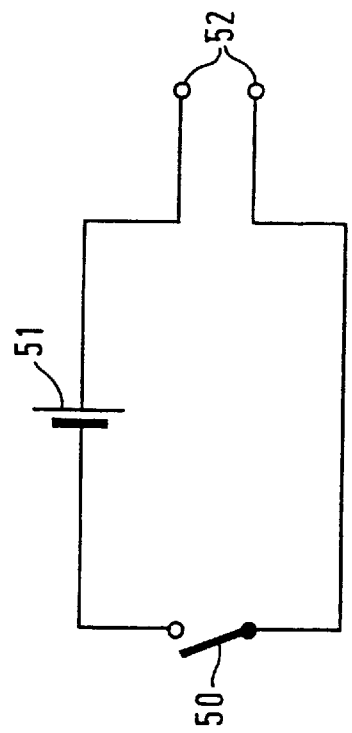
Figure 8:
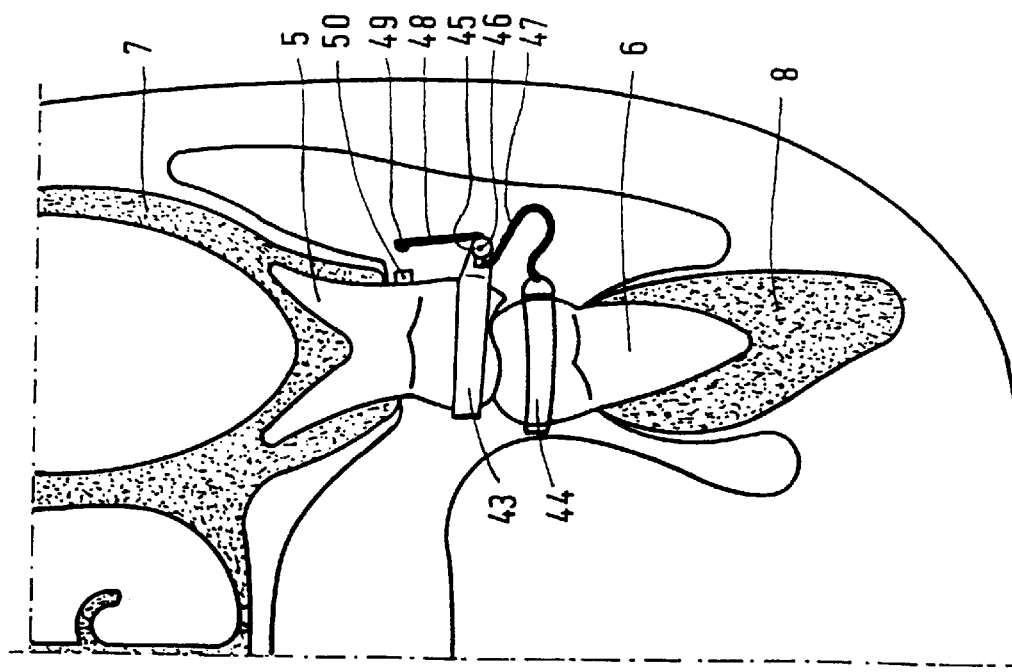
FIG. 8 diagrammatically shows an embodiment wherein the thickened part of the bar-shaped element co-operates with an electric/electronic component which is incorporated in a circuit as shown in FIG. 9.

FIG. 8 diagrammatically shows an embodiment similar to the one shown in FIG. 4, with the difference that a component 50 is provided at the location where thickened end 49 of bar-shaped element 48 makes contact with the tooth. This component may be a switch element which forms part of an electric circuit. An example of such a circuit is shown in FIG. 9. In addiction to said switch element 50, said circuit also comprises a voltage source 51, a battery, for example, and electrodes 52, which deliver an electric shock signal to a sensitive place in the mouth cavity in the closed condition of circuit element 50. Instead of being provided with electrodes 52, it is also possible under certain circumstances for said electric circuit to be provided with means which generate a sound signal or a vibration signal, which functions to warn the user that it is not desirable to open his jaws any further.

Figure 10:
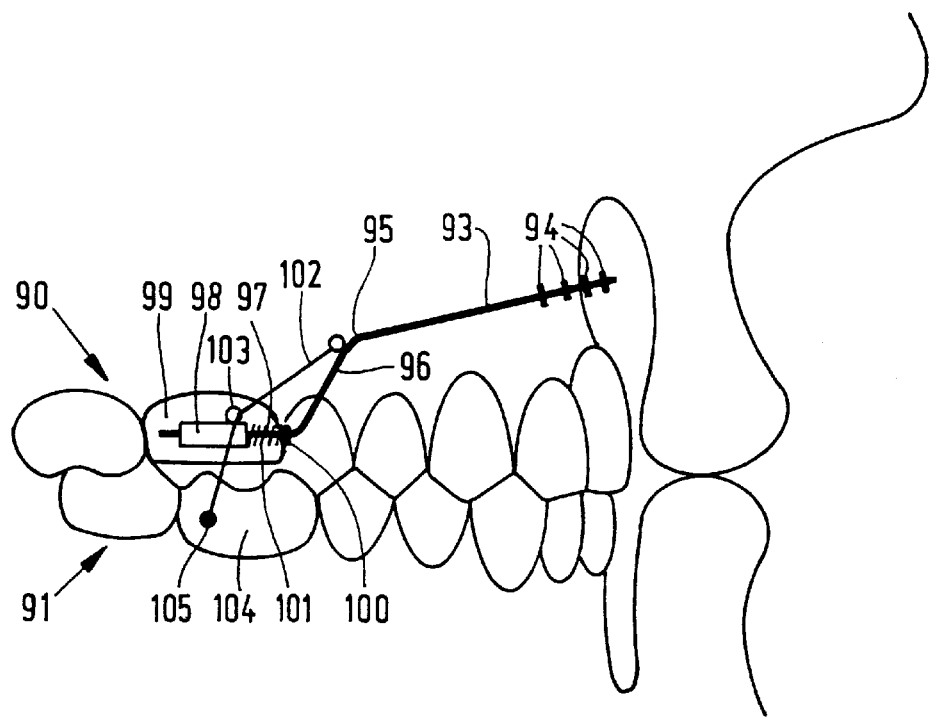
FIGS. 10 and 11 diagrammatically show an embodiment wherein a wire-like element is provided around the upper jaw, which element can be tensioned by opening of the jaws.
Figure 11:
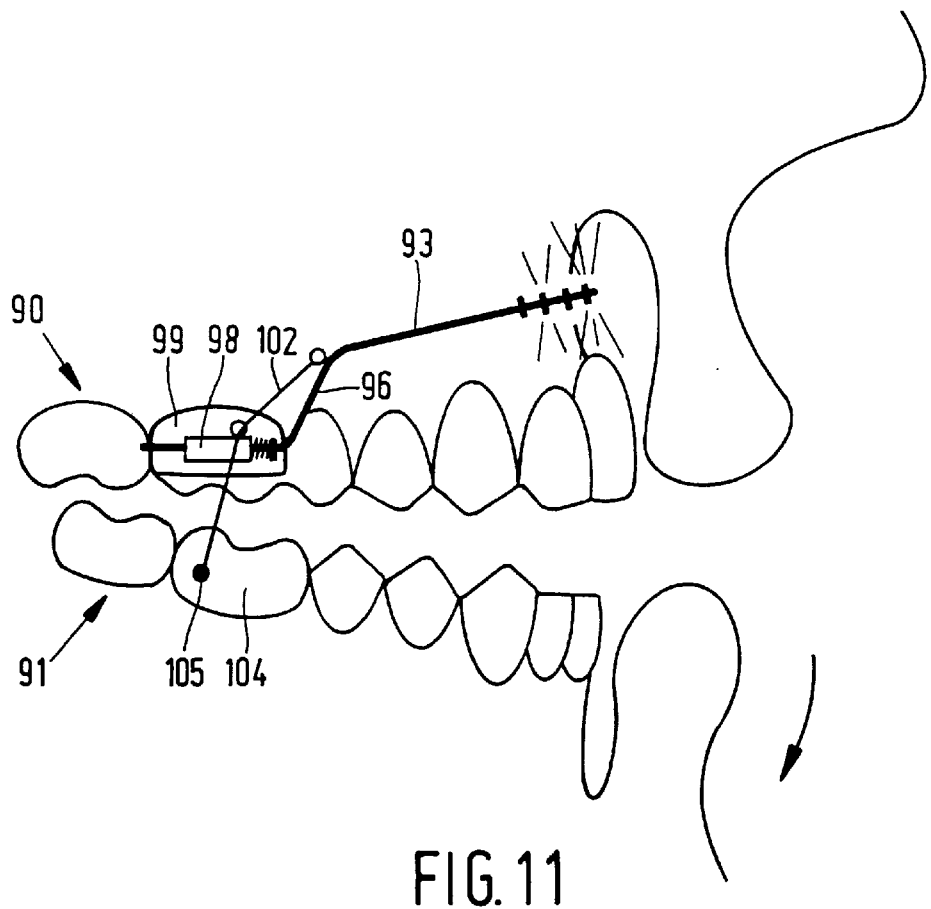

FIG. 10 and 11 are diagrammatic side views of lower teeth 90 and upper teeth 91 in the closed and the opened position of the jaws respectively. A wire-like element 93 is turned around the upper jaw, which element extends from one side to the other (not shown). Wire-like element 93 is thereby provided with local thickenings 94. Wire-like element 93 is bent at 95 and extends via a part 96 to a part 97, which is guided in a tubular guide 98, which is attached to a tooth 99 forming part of upper teeth 90. A stop 100 is provided on part 97, with a spring 101 being present between stop 100 and tube 98. The spring exerts a force on stop 100, such that element 93 will no longer be in contact with the jawbone. A flexible cord 102 of metal, textile, plastic material, etc. is attached to wire-like element 93 at 95. Said cord 102 extends via an eye 103 on tube 98 to a tooth 104 of the lower jaw, to which tooth said cord is attached by suitable means. The same construction as the one described above is used on the other side of the jaws.

When the jaws are opened, as is shown in FIG. 11, the lower teeth will pull at the end 105 of cord 102. As a result of this a pulling force will also be exerted on point 95 of wire-like element 93, so that said element is pulled against the front side of the jaw, which leads to a sensation of pressure or pain, which functions to remind the user not to open his jaw any further. Said sensation of pressure or pain is furthermore intensified by the local thickenings 94. When wire-like element 93 is tightened, part 97 thereof will be moved further along tubular guide 98, whereby spring 101 is tensioned. When the jaws are subsequently closed, spring 101 will be released again, as a result of which wire-like element 93 will no longer press against the jaw.

From the above it will be apparent that the invention provides a method and means for influencing the amount of food being ingested by humans by reducing the capacity of the mouth cavity. This makes it possible to fight obesity and reduce any extra weight that may be present. It has become apparent that the result of this method is noticeable after a very short time. After the intended weight has been reached, the means for carrying out the method may be removed from the mouth cavity, whereby it has become apparent that the user of said means will benefit from the method for quite some time thereafter. If after some time it should become apparent that nevertheless the weight is increasing again, said means may be placed in the mouth cavity again.

From the above it will be apparent that the invention provides a method and means for fighting obesity, whereby the user can continue to eat in a normal manner, albeit at a slightly slower rate than before, so that the method will hardly spoil the user's pleasure in eating, if at all.

Although the elements which are placed in the mouth on either side thereof are shown in the form of separate elements in the drawings, it is also possible to interconnect the elements in question by means of a brace-like element extending around the upper jaw and the lower jaw. Although only one half of the mouth cavity is shown in a few Figures, it will be apparent that the means in question are also provided on the other side of the mouth cavity.

What is claimed is:

1. A device for influencing the ingestion of food via the mouth cavity of humans, said device comprising:

connecting means adapted to be provided between the upper jaw and the lower jaw for impeding the opening movement of the lower jaw, said connecting means co-operate with further means present in the mouth cavity generating a signal when the lower jaw is opened beyond a predetermined limit, as a result of which the lower jaw is prevented from opening any further, said further means being mechanical means for generating at least one of a sensory stimulus and a pain stimulus at a sensitive place in the mouth cavity.

2. A device according to claim 1, wherein said further means includes electric/electronic means, by which one of a sound signal, a vibration signal and a pain signal is generated.

3. A device according to claim 1, wherein said connecting means are made up of one or more bar-shaped elements, each bar-shaped element is provided, at least at one end, with a flanged part or a thickening, which fits in a space between jawbone and cheek, and an element which engages around each bar-shaped element and which is capable of sliding movement over said bar-shaped element and which is adapted to be provided on at least one of the upper and lower teeth, all this in such a manner that when the lower jaw is opened, said flanged part or said thickening is pressed against a sensitive part of the jaw.

4. A device according to claim 3, wherein each bar-shaped element is adapted to be fixed to one of the upper teeth and the lower teeth with one end, and is provided with said flanged part or said thickening at the other end of said bar-shaped element.

5. A device according to claim 3, wherein said flanged part or said thickening co-operates with an electric/electronic component adapted to be provided on the teeth.

6. A device according to claim 5, wherein said electric/electronic component is a switch element, which is-incorporated in an electric circuit comprising a voltage source and electrodes for producing an electric shock adapted to be delivered to a sensitive part of the mouth cavity.

7. A device according to claim 5, wherein said electric/electronic component is a switch element, which is incorporated in an electric circuit comprising a voltage source and means for generating at least one of a sound signal and a vibration signal.

8. A device according to claim 5, wherein said electric/electronic component is made up of a stack of one or more piezo-electric plates, which generate an electric voltage when a pressure is exerted thereon, which voltage is adapted to be applied to a sensitive part of the mouth cavity.

9. A device according to claim 1, wherein said connecting means are made up of at least one flexible cord or wire, which is adapted to be fixed to one of the lower teeth and the upper teeth with one end, and in that said further means are made up of at least one element, to which the other end of said cord or said wire is connected in such a manner that the tensioned cord or wire is adapted to press the element against one of the upper jaw and the lower jaw when the jaws are opened.

10. A device according to claim 9, wherein said at least one element is a pivoting element adapted to be provided on one of said upper teeth and said lower teeth, to which said cord or said wire is connected with the other end of the pivoting element and which is provided with a bar-shaped part, which exhibits a flanged part or a thickening at the end of the bar-shaped element which is adapted to be moved towards the jawbone by the pivoting movement of the element.

11. A device according to claim 9, wherein said at least one element is at least one wire-like or strip-like element adapted to be provided around the upper jaw or the lower jaw, said element on either side of the mouth cavity being passed over guide elements adapted to be attached to the upper teeth or the lower teeth, and furthermore adapted to be connected to the upper teeth or the lower teeth with the ends of said element.

12. A device according to claim 11, wherein said wire-like or strip-like element is provided with local thickenings.

13. A device suitable for influencing the ingestion of food via the mouth cavity of humans, comprising connecting means adapted to be provided between an upper jaw and a lower jaw, said connecting means co-operating with two elements which are adapted to be connected to the teeth of the upper and lower jaw, said connecting means impeding an opening movement of the lower jaw, said connecting means co-operating with further means present in the mouth cavity generating a signal when the lower jaw is opened beyond a predetermined limit, as a result of which the lower jaw is prevented from opening any further, -said further means comprising mechanical means for generating at least one of a sensory stimulus and a pain stimulus at a sensitive place in the mouth cavity.

14. A device according to claim 13, wherein said further means includes electric/electronic means, by which one of a sound signal, a vibration signal and a pain signal is generated.

15. A device according to claim 13, wherein said connecting means consist of a bar-shaped element, which is provided with a flanged part or a thickening at least at one of the ends of said bar-shaped element and wherein at least one of the two said elements which are adapted to be connected to the teeth of the upper or lower jaw, located near the end of the bar-shaped element, provided with a flanged part or thickening, is capable of sliding movement over said bar.

16. A device according to claim 15, wherein the bar-shaped element is provided with a flanged part or a thickening at only one of the ends of said bar-shaped element, the other end being fixed to one of said connecting elements, which is adapted to be connected to the teeth of the upper and lower jaw.

17. A device according to claim 15, wherein said thickening or said flanged part co-operates with an electric/electronic component which is adapted to be provided on the teeth.

18. A device according to claim 17, wherein said electric/electronic component is a switch element, which forms part of an electric circuit comprising a voltage source and electrodes for delivering an electric shock to a sensitive part of the mouth cavity.

19. A device according to claim 17, wherein said electric/electronic component is a switch element, which forms part of an electric circuit comprising a voltage source and means for generating at least one of a sound signal and a vibration signal.

20. A device according to claim 17, wherein said electric/electronic component is a piezo-electric component, which generates an electric voltage when a pressure is exerted thereon.

21. A device according to claim 13, wherein said connecting means consist of at least one flexible cord or wire, which is provided at both ends with a fastening element, which is adapted to be connected to the teeth of the lower jaw or the upper jaw, whereby one of said fastening elements is provided with a pivoting element, to which said flexible cord or wire is attached with one end, and which is furthermore provided with a bar-shaped element, which exhibits a thickening or flanged part at the end of said bar-shaped element, which is adapted to be moved into contact with the jawbone by the pivoting movement of said pivoting element.

22. A device according to claim 21, wherein said cord or wire is deformable in its longitudinal direction, and is made of a memory material.

23. A device according to claim 13, wherein said connecting means consist of a flexible strip or wire comprising a part which is adapted to be provided on one of said upper or lower jaw, whereby sliding elements are provided around said wire or strip on either side of said part, which sliding elements are adapted to be connected to the teeth of said one jaw on which said part is provided, and whereby the ends of said strip or wire are provided with further connecting means which are adapted to be connected to the teeth of the other jaw.

24. A device according to claim 23, wherein the part of said strip or wire that is adapted to be provided around the upper jaw or the lower jaw, is provided with one or more local thickenings.

25. A device for influencing the ingestion of food via the mouth cavity of humans, said device comprising:

connecting means adapted to be provided between the upper jaw and lower jaw for impeding the movement of the lower jaw, said connecting means co-operate with further means present in the mouth cavity generating a signal when the lower jaw is opened beyond a predetermined limit as a result of which the lower jaw is prevented from opening any further, said connecting means being made up of one or more bar-shaped elements, each bar-shaped element being provided, at least at one end, with a flanged part or a thickening, which is adapted to fit in a space between jawbone and cheek, and an element which engages around each bar-shaped element and which is capable of sliding movement over said bar-shaped element and which is adapted to be provided on at least one of the upper and lower teeth, all this is such a manner that when the lower jaw is opened, said flanged part or said thickening is pressed against a sensitive part of the jaw.

26. A device for influencing the ingestion of food via the mouth cavity of humans, said device comprising:

connecting means adapted to be provided between the upper jaw and the lower jaw for impeding the movement of the lower jaw, said connecting means co-operate with further means present in the mouth cavity generating a signal when the lower jaw is opened beyond a predetermined limit, as a result of which the lower jaw is prevented from opening any further, said connecting means being made up of at least one flexible cord or wire, which is adapted to be fixed to one of the lower teeth and the upper teeth with one end, and in that said further means are made up of at least one element, to which the other end of said cord or said wire is connected in such a manner that the tensioned cord or wire is adapted to press the element against one of the upper jaw and the lower jaw when the jaws are opened.

27. A device suitable for influencing the ingestion of food via the mouth cavity of humans, comprising:

connecting means adapted to be provided between an upper jaw and a lower jaw, said connecting means co-operating with two elements which are adapted to be connected to the teeth of the upper and lower jaw, said connecting means impeding an opening movement of the lower jaw, said connecting means co-operating with further means present in the mouth cavity generating a signal when the lower jaw is opened beyond a predetermined limit, as a result of which the lower jaw is prevented from opening any further, said connecting means consisting of a bar-shaped element, which is provided with a flanged part or a thickening at least at one of the ends of said bar-shaped element and wherein at least one of the two said elements which are adapted to be connected to the teeth of the upper or lower jaw, located near the end of the bar-shaped element, provided with a flanged part or thickening, is capable of sliding movement over said bar.

28. A device suitable for influencing the ingestion of food via the mouth cavity of humans, comprising:

connecting means adapted to be provided between an upper jaw and a lower jaw, said connecting means co-operating with two elements which are adapted to be connected to the teeth of the upper and lower jaw, said connecting means impeding an opening movement of the lower jaw, said connecting means co-operating with further means present in the mouth cavity generating a signal when the lower jaw is opened beyond a predetermined limit, as a result of which the lower jaw is prevented from opening any further, said connecting means consisting of at least one flexible cord or wire, which is provided at both ends with a fastening element, which can be connected to the teeth of the lower jaw or the upper jaw, whereby one of said fastening elements is provided with a pivoting element, to which said flexible cord or wire is attached with one end, and which is furthermore provided with a bar-shaped element, which exhibits a thickening or flanged part at the end of the bar-shaped element which is adapted to be moved into contact with the jawbone by the pivoting movement of said pivoting element.

29. A device suitable for influencing the ingestion of food via the mouth cavity of humans, comprising:

connecting means adapted to be provided between an upper jaw and a lower jaw, said connecting means co-operating with two elements which are adapted to be connected to the teeth of the upper and lower jaw, said connecting means impeding an opening movement of the lower jaw, said connecting means co-operating with further means present in the mouth cavity generating a signal when the lower jaw is opened beyond a predetermined limit, as a result of which the lower jaw is prevented from opening any further, said connecting means consisting of a flexible strip or wire comprising a part which is adapted to be provided on the upper or lower jaw, whereby sliding elements are provided around said wire or strip on either side of said part, which sliding elements are adapted to be connected to the teeth of said one jaw on which said part is provided, and whereby the ends of said strip or wire are provided with further connecting means which are adapted to be connected to the teeth of the other jaw.

* * * * *